United States Patent [19]
Hipp

[11] Patent Number: 5,706,143
[45] Date of Patent: Jan. 6, 1998

[54] OPTICAL DEVICE

[75] Inventor: Klaus-Peter Hipp, Bretten, Germany

[73] Assignee: Richard Wolf GmbH, Knittlingen, Germany

[21] Appl. No.: 663,621

[22] Filed: Jun. 14, 1996

[30] Foreign Application Priority Data

Jun. 14, 1995 [DE] Germany .................. 195 21 654.7

[51] Int. Cl.⁶ ................................................ G02B 7/02
[52] U.S. Cl. ................ 359/824; 359/827; 359/694; 359/903; 396/17; 396/144; 126/4
[58] Field of Search ......................... 359/814, 813, 359/827, 824, 823, 694, 700, 903; 126/4; 396/144, 17

[56] References Cited

U.S. PATENT DOCUMENTS

| 4,828,360 | 5/1989 | Maruyama | 359/824 |
| 5,078,472 | 1/1992 | Sugawara | 359/824 |
| 5,359,992 | 11/1994 | Hori et al. | 359/903 |
| 5,432,639 | 7/1995 | Sakamoto | 359/823 |

FOREIGN PATENT DOCUMENTS 0454325  10/1991  European Pat. Off. .

*Primary Examiner*—Loha Ben
*Attorney, Agent, or Firm*—Cohen, Pontani, Lieberman & Pavane

[57] ABSTRACT

A magnetically actuated optical focusing device is provided. The focusing device comprises a housing with an optical component being displaceably and rotatably arranged therein. The optical component is ferromagnetically coupled, via an internal magnet arranged thereon, to an external magnet arranged outside of the housing, the external magnet being fixed to a focusing ring which is rotatably mounted on the housing. When the focusing ring is rotated, the ferromagnetic attraction between the magnets is sufficient to drive the internal magnet through a helical channel defined on the internal surface of the housing, thus causing the optical component to be longitudinally displaced within the housing. The helical channel exerts sufficient restraining force on the inner magnet so that the inner magnet remains in a particular position along the channel even if the ferromagnetic coupling between the magnets is broken down. Thus, any unintended adjustment of the optical component by an external force is reliably prevented.

9 Claims, 2 Drawing Sheets

OPTICAL DEVICE

BACKGROUND OF THE INVENTION

1. Field of the Invention

The invention relates to optical focusing devices, and in particular to a hermetically sealed magnetically actuated optical focusing device.

2. Description of the Related Art

Magnetically actuated optical focusing devices are typically used in the medical field as an objective between a proximal end of an endoscope and a video camera. For hygienic purposes, such devices frequently undergo disinfection treatment. The housing of a typical optical focusing device is therefore hermetically sealed with the exception of a terminal viewing window on an end side. The housing typically contains an internally disposed optical component, typically consisting of one or more lenses positioned in a lens holder, and an externally disposed focusing component. For focusing on an image, it is necessary to move the optical component in the direction of an optical axis of the housing. The transmission of force between the optical component and focusing component is typically effected magnetically through the wall of the housing. Thus, the optical component is provided with an externally mounted first magnet, while the focusing component is provided with a correspondingly cooperating similar sized second magnet. In order to focus on an image, the focusing component is guided by a user in a helical path in the form of a thread or a recess defined in the external wall of the housing so that as the second magnet is translated along the helical path, the first magnet follows the second magnet along the path by ferromagnetic force coupling the first magnet to the second magnet through the housing wall, and thus causes the optical component to also move longitudinally in the direction of the optical axis. Optical focusing devices of this type are described in the German utility model DE-U-8810044 and U.S Pat. No. 5,359,992.

The main disadvantage of previously known magnetically actuated optical focusing devices is that a sudden shaking or knocking of a typical focusing device may cause the non-positive ferromagnetic connection between the first and the second magnets to break down, thus causing the optical component adjustably disposed within the housing to become freely movable. In addition, the optical component may be displaced by its own weight when the optical focusing device is positioned at a steep angle, especially if the optical component includes several heavy lenses. If the optical component becomes freely movable, the non-positive ferromagnetic connection between the magnets must first be manually restored and the focusing adjustment must then be renewed, which is an extremely inconvenient task during a medical procedure.

A further problem common in previously known magnetically actuated optical focusing devices is the relatively small magnitude of the ferromagnetic retention force between the first and second magnets. This problem occurs because in previously known magnetically actuated optical focusing devices, the first and second magnets are typically polarized in the direction of the optical axis.

SUMMARY OF THE INVENTION

It is the object of the invention to develop a magnetically actuated optical focusing device that is capable of reliably preventing an adjustment of an optical component of its own accord, and also reliably preventing breakdown of a ferromagnetic cooperation between a pair of actuating magnets even in the case of shock or a sudden force applied to the focusing device.

The magnetically actuated optical focusing device in accordance with the present invention includes a generally cylindrical housing having an internal sleeve with a substantially helical channel defined in the internal sleeve. A generally cylindrical optical component is displaceably and rotatably disposed internal to the housing. The optical component consists of a cylindrical lens holder and one or more lenses. The optical component has an externally disposed first magnet and is positioned within the housing so that the first magnet is disposed within the helical channel. The helical channel exerts a sufficient restraining force on the first magnet, such that the first magnet is not capable of moving within the channel of its own accord and must be forcibly guided through the channel if movement is desired. The circumferential angle of the helical channel is preferably no more than about 270°. The optical focusing device also includes a focusing ring rotably disposed external to the housing. The focusing ring includes a second magnet disposed on its internal surface such that the second magnet is ferromagnetically coupled to the first magnet through a housing wall. To focus on an image, the focusing ring is axially rotated so that the second magnet forcibly guides the first magnet along the helical channel by ferromagnetic attraction, causing the first magnet to be longitudinally translated with respect to the focusing ring, and thus causing the optical component to also be longitudinally displaced relative to the focusing ring along a central axis of the housing.

The helical shaped path is preferably arranged with a pitch such that for any displacing of the optical component in the direction of the optical axis is only possible by deliberate manipulation of the focusing ring. The first magnet is preferably a round magnet, while the second magnet is preferably a rectangular magnet so that the polarization of each magnet is directed in a radial manner. Radial polarization results in a relatively strong magnetic field, therefore achieving a high retention force. The length of the second magnet in the axial direction of the focusing device is preferably approximately equal to the maximum displacement distance of the first magnet in the axial direction of the focusing device, which causes the first magnet to be in constant ferromagnetic communication with the second magnet at any position along the helical path. The ratio of surface areas of the first and second magnet surfaces which face one another may be chosen from a range of 1:2 to 1:3, and is preferably about 1:2.5. This ratio further increases the ferromagnetic retention force between the first and the second magnets.

Thus, although the optical component is rotably and axially displaceably mounted within the housing, movement of the optical component may only be accomplished by an application of rotable force to the focusing ring and not by a knock, a shake or other external mechanical influence exerted upon the focusing device. Even if the ferromagnetic cooperation between the first and the second magnets is interrupted for some unforeseen reason, the optical component would remain in a particular position due to the restraining force of the helical channel exerted on the first magnet.

Because the axial movement of the optical component is limited to the axial distance of the helical channel, there is a danger that a freely rotating focusing ring may loose ferromagnetic contact with the optical component once the optical component reaches an end of the helical channel.

since the focusing ring may continue rotation. Thus, a stop detent is positioned on the housing to limit the rotation of the focusing ring such that the focusing ring is prevented from rotating in a first direction when the optical component is at the beginning of the helical channel, and prevented from rotating in a second direction just before the optical component reaches the end of the helical channel. Thus, the second magnet of the focusing ring is forced to be in constant ferromagnetic communication with the first magnet of the optical component.

Other objects and features of the present invention will become apparent from the following detailed description considered in conjunction with the accompanying drawings. It is to be understood, however, that the drawings are designed solely for purposes of illustration and not as a definition of the limits of the invention, for which reference should be made to the appended claims.

DETAILED DESCRIPTION OF A PRESENTLY PREFERRED EMBODIMENT

Although the present invention is described with reference to a specific embodiment of a magnetically actuated optical focusing device for connection of a video camera to a medical instrument such as an endoscope, it should be understood that the magnetically actuated optical focusing of the present invention may be adapted for use in other image focusing applications requiring a hermetically sealed focusing device.

Figure 1:
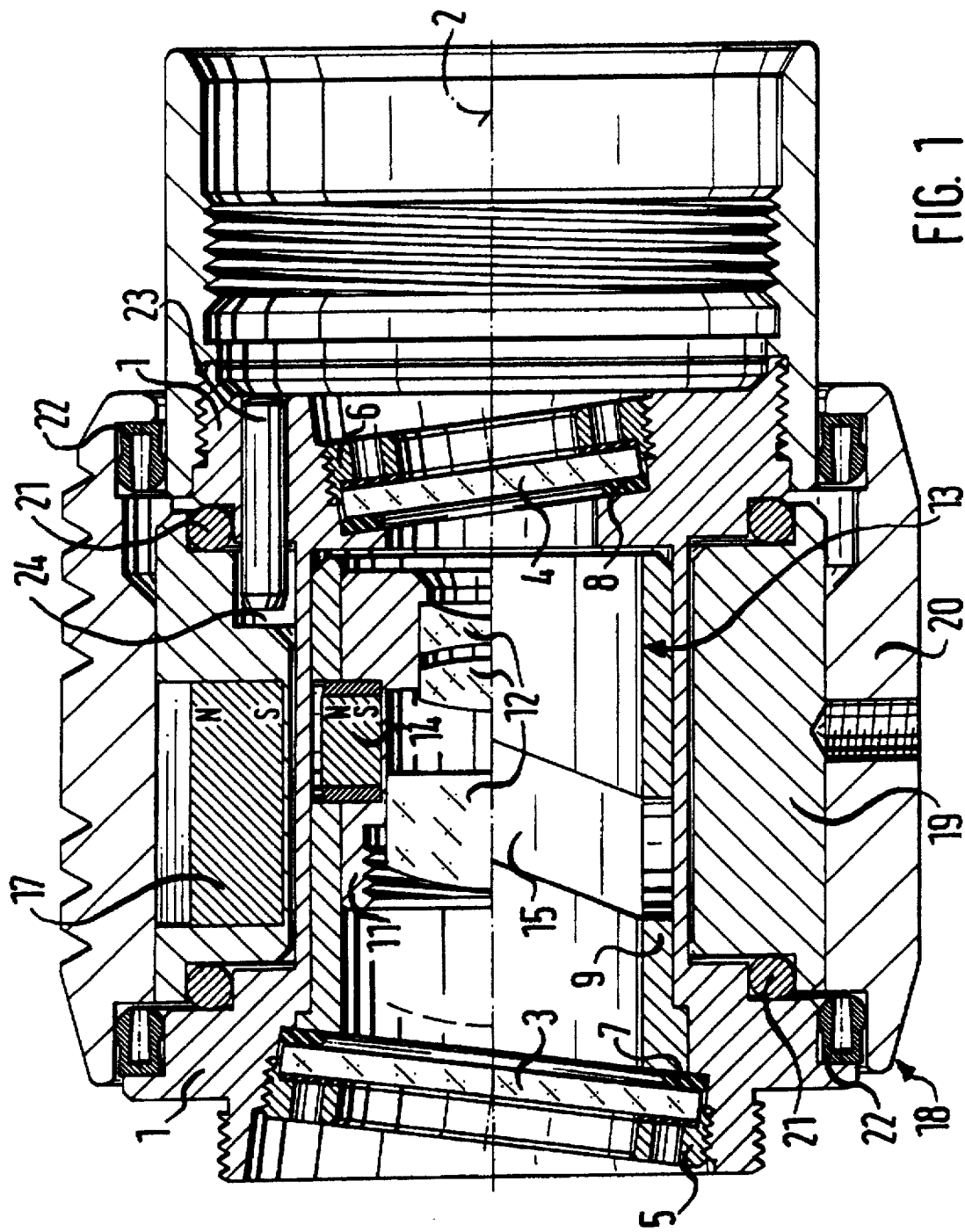
FIG. 1 is a longitudinal schematic view of a magnetically actuated optical focusing device in accordance with the present invention.
Figure 2:
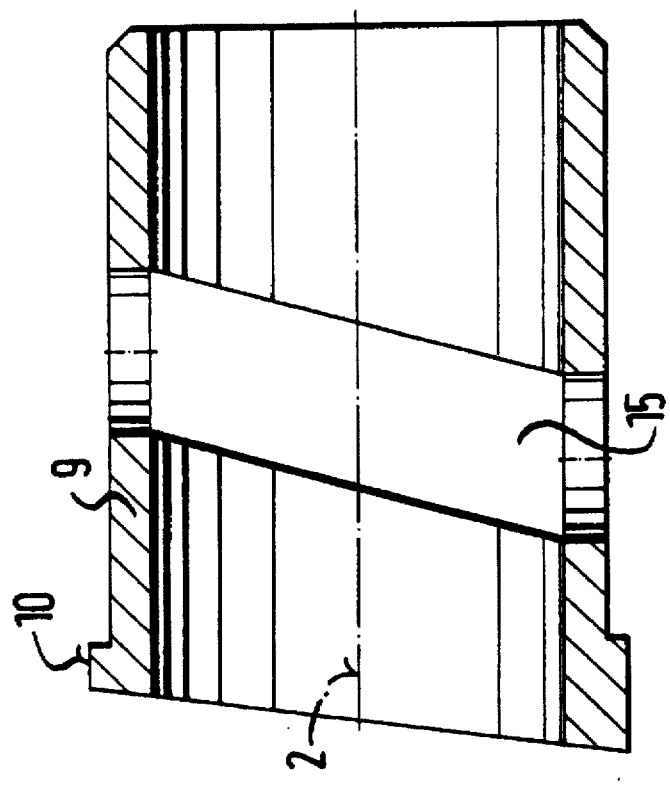
FIG. 2 is a longitudinal schematic view of a sleeve of the optical focusing device of FIG. 1.
Figure 3:
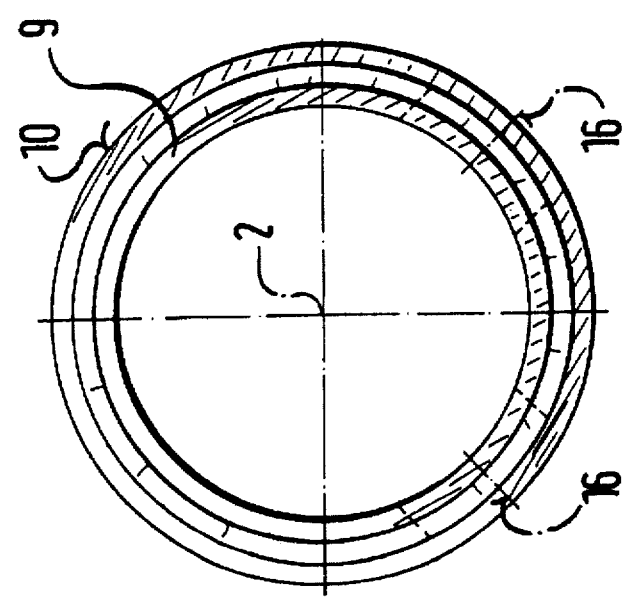
FIG. 3 is a front schematic view of the sleeve of FIG. 2.

The magnetically actuated optical focusing device of the present invention comprises a generally cylindrical hollow housing 1 having an optical axis 2 longitudinally defined through its center and having terminal windows 3 and 4 at each end, which are positioned at a slight incline with respect to the housing. The terminal windows 3 and 4 are connected to the housing 1 in a pressure tight manner by way of threaded rings 5 and 6, respectively, into which O-rings 7 and 8, respectively, are incorporated. The threaded ring 5 also retains a cylindrical sleeve 9 which is longitudinally disposed within the housing 1. The sleeve 9 is longitudinally fixed in the direction of the axis 2, and is also rotationally fixed by way of the inclined arrangement of the terminal window 3 and an accordingly formed flange 10 of the sleeve 9. The sleeve 9 includes a helical channel 15 defined in its internal surface and arranged about the axis 2. The preferable pitch of the channel 15 is shown in FIG. 2. The channel 15 extends over a circumference of the sleeve 9 of about 270°, as can be seen from FIG. 3, which shows a pair of ends 16 of the channel 15.

Internal to the sleeve 9, a mounting 11 for a focusing lens group 12 is axially displaceably and rotatably mounted. The mounting 11 accommodates a group of lenses, although a single lens may be used as well. An optical component formed by the mounting 11 and the lens group 12 is given the reference numeral 13 which is not shown on the drawing.

On its outer circumference, the mounting 11 includes a channel in which a first magnet 14 is positioned. The magnet 14 is preferably round and is preferably radially polarized. The magnet 14 rises above the outer surface of the mounting 11 and protrudes into the channel 15 in which the first magnet 14 may be forcibly guided. The width of the channel 15, corresponds approximately to the diameter of the first magnet 14.

The housing 1, in the section over which the channel 15 extends, comprises a thin wall region. In the thin wall region, a second magnet 17 is rotatably arranged external to the housing 1 about the axis 2. The second magnet 17 is preferably rectangular and is preferably radially polarized. The ratio of surface areas of the first magnet 14 and the second magnet 17 surfaces which face one another may be chosen from a range of 1:2 to 1:3, and is preferably about 1:2.5. The second magnet 17 preferably has a length in the direction of the axis 2 approximately equal to the maximum linear displacement path of the optical component 13 and has a width which is approximately equal to the diameter of the first magnet 14.

A focusing ring 18 is rotably disposed around the housing 1 about the axis 2, but is axially fixed. The focusing ring 18 includes an internal supporting ring 19 and an outside overlapping adjusting ring 20. The adjusting ring 20 is isolated from the housing 1 at its end sides by means of lip seals and split washers 22. The lip seals and washers 22 protect from dirt and disinfection agents which may otherwise enter into the area between the supporting ring 19 and the housing 1.

The second magnet 17 is mounted in an internal recess of the supporting ring 19. The focusing ring 18 is mounted on the housing 1 so as to position the second magnet 17 over the thin wall region of the housing 1, through which it may achieve a non-positive ferromagnetic connection with the first magnet 14.

The rotational movement of the focusing ring 18 in clockwise and counterclockwise directions is limited by a peg 23, which is disposed in the housing 1 parallel to the axis 2, and which forms a stop detent cooperating with a corresponding channel 24 on the inside edge of the supporting ring 19. The channel 24 extends over about 265° of the circumference of the supporting ring 19, so that the possible rotational movement of the focusing ring 18 is smaller than the 270° circumferential extension of the helical channel 15.

The focusing of an image is accomplished by turning the adjusting ring 20, thus causing the supporting ring 19, with the second magnet 17 arranged on its inner side, to rotate about the outer circumference of the housing 1. The ferromagnetic attraction between the first magnet 14 and the second magnet 17 causes the rotating second magnet 17 to forcibly drive the first magnet 14 along the helical channel 15, thus causing the optical component 13 to axially rotate but also to longitudinally move along the axis 2 thereby accomplishing the focusing function. Because the second magnet 17 is as long as the total displacement path of the first magnet 14, the ferromagnetic attraction between the first and the second magnets 14 and 17, respectively, remains constant regardless of the radial position of the second magnet 17.

Thus, while there have shown and described and pointed out fundamental novel features of the invention as applied to a preferred embodiment thereof, it will be understood that various omissions and substitutions and changes in the form and details of the devices illustrated, and in their operation, may be made by those skilled in the art without departing from the spirit of the invention. For example, it is expressly intended that all combinations of those elements and/or method steps which perform substantially the same function in substantially the same way to achieve the same results are within the scope of the invention. It is the intention, therefore, to be limited only as indicated by the scope of the claims appended hereto.

I claim:

1. An optical device comprising:

a housing (1) having a central axis;

an optical component (13) displaceably and rotatably arranged within said housing;

an internal magnet (14) connected to said optical component (13) and disposed for sliding movement within said housing along a helical channel;

an external component (18) movably mounted on the outside of said housing (1);

an external magnet (17) attached to said external component (18) and arranged for magnetic interaction with said internal magnet (14) so that upon movement of said external magnet (17) said internal magnet (14) is moved along said helical channel.

2. The optical device of claim 1, wherein the internal magnet is substantially round, and wherein the external magnet is substantially rectangular.

3. The optical device of claim 1, wherein the helical channel extends for a predetermined distance along the central axis of said housing, and wherein said external magnet has a length substantially equal to the predetermined distance.

4. The optical device of claim 1, wherein a first surface of said internal magnet is ferromagnetically coupled to a second surface of said external magnet through said housing, and wherein a ratio of surface area of said first surface to surface area of said second surface is selected from a range of 1:2 to 1:3.

5. The optical device of claim 1, wherein said helical channel extends over a circumferential angle of the housing of approximately 270 degrees.

6. The optical device of claim 1, wherein rotational movement of said external component (18) is limited by a stop detent so as to ensure constant ferromagnetic contact between said internal and said external magnets.

7. The optical device of claim 1, wherein said internal and said external magnets are polarized radially relative to the central axis of said housing.

8. The optical device of claim 1, wherein said optical component (13) comprises a lens holder and at least one optical lens disposed within said lens holder.

9. The optical device of claim 1, wherein focusing of an image by said optical component (13) is accomplished by rotating said external component (18) in at least one of a clockwise and a counterclockwise direction.

* * * * *